(12) United States Patent
Lerman

(10) Patent No.: US 9,033,896 B2
(45) Date of Patent: May 19, 2015

(54) OBTAINING A TISSUE SAMPLE

(75) Inventor: Amir Lerman, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 1984 days.

(21) Appl. No.: 11/774,804

(22) Filed: Jul. 9, 2007

(65) Prior Publication Data

US 2008/0015466 A1 Jan. 17, 2008

Related U.S. Application Data

(60) Provisional application No. 60/830,443, filed on Jul. 13, 2006.

(51) Int. Cl.
*A61B 10/06* (2006.01)
*A61B 17/12* (2006.01)
*A61B 18/14* (2006.01)

(52) U.S. Cl.
CPC ........... *A61B 10/06* (2013.01); *A61B 17/12022* (2013.01); *A61B 18/1492* (2013.01)

(58) Field of Classification Search
CPC ............. A61B 10/06; A61B 17/12022; A61B 18/1492
USPC .................. 600/564, 439, 18, 437, 561, 567; 604/914, 96.01; 623/2.1
See application file for complete search history.

(56) References Cited

U.S. PATENT DOCUMENTS

| | | | |
|---|---|---|---|
| 5,158,529 A * | 10/1992 | Kanai | 600/18 |
| 5,431,628 A | 7/1995 | Millar | |
| 5,715,832 A | 2/1998 | Koblish et al. | |
| 5,779,646 A | 7/1998 | Koblish et al. | |
| 5,836,886 A | 11/1998 | Itoigawa et al. | |
| 6,004,275 A | 12/1999 | Billiet | |
| 6,409,674 B1 | 6/2002 | Brockway et al. | |
| 6,602,270 B2 * | 8/2003 | Leschinsky et al. | 606/194 |
| 6,689,062 B1 * | 2/2004 | Mesallum | 600/439 |
| 6,723,053 B2 | 4/2004 | Ackerman et al. | |
| 6,935,999 B2 | 8/2005 | Schock et al. | |
| 6,974,422 B1 | 12/2005 | Millar | |
| 7,373,207 B2 * | 5/2008 | Lattouf | 607/130 |
| 2004/0231664 A1 * | 11/2004 | Lurie et al. | 128/200.11 |
| 2004/0254483 A1 | 12/2004 | Zdeblick et al. | |
| 2005/0197692 A1 * | 9/2005 | Pai et al. | 623/2.1 |

\* cited by examiner

*Primary Examiner* — Max Hindenburg

(74) *Attorney, Agent, or Firm* — Fish & Richardson P.C.

(57) ABSTRACT

Some embodiments of a biopsy system are configured to obtain a sample of tissue from an internal body site, such as a portion of myocardial tissue from a heart chamber wall. The biopsy system may include a catheter device having tissue collection jaws and an inflatable balloon disposed along a distal portion. Also, the biopsy system may include a pressure sensor device to detect the pressure within the heart chamber in which the tissue collection jaws are disposed.

19 Claims, 3 Drawing Sheets

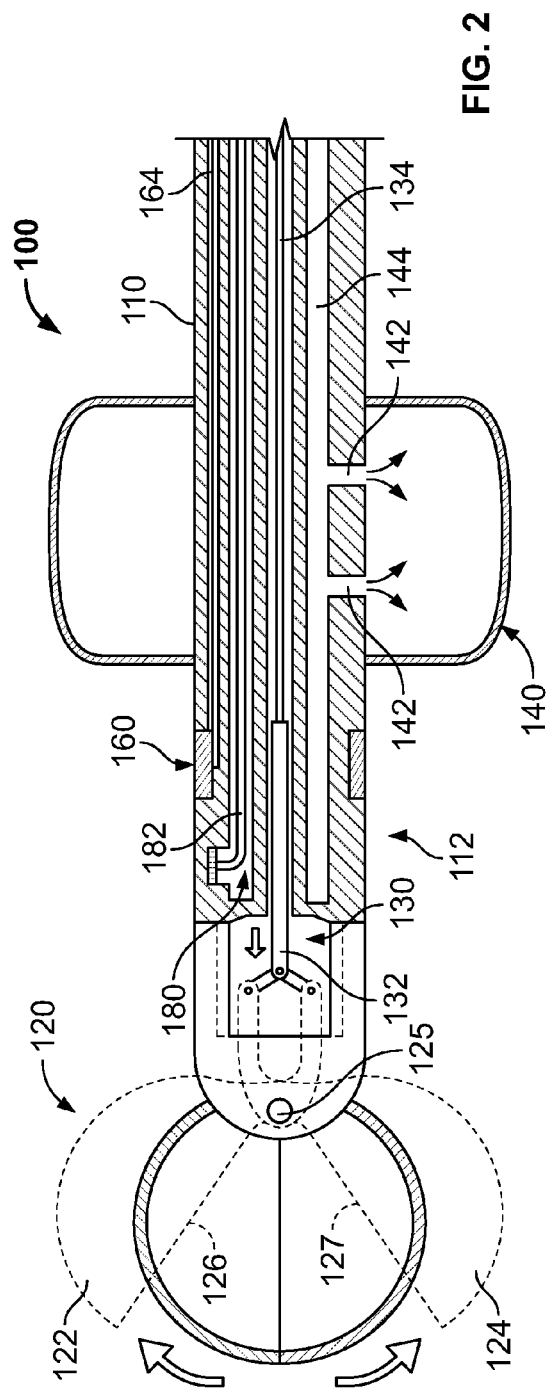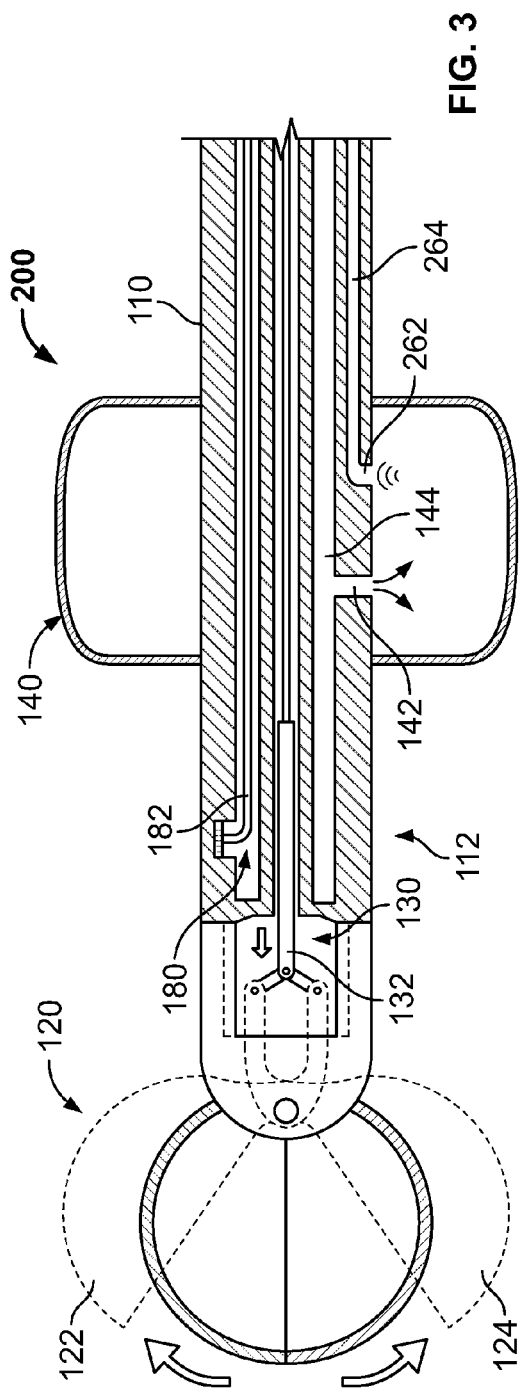

OBTAINING A TISSUE SAMPLE

CROSS-REFERENCE TO RELATED APPLICATIONS

This application claims priority to U.S. provisional application Ser. No. 60/830,443, filed Jul. 13, 2006. The entire contents of this earlier application is incorporated herein by reference.

TECHNICAL FIELD

This document relates to systems and methods for performing a biopsy at an internal body site, for example, obtaining a myocardial tissue sample from a heart chamber wall.

BACKGROUND

Biopsy instruments can be used to obtain samples of tissue from the body of a human or other animal. In some circumstances, the biopsy instruments are delivered into the patient's body to retrieve a tissue sample from an internal site. For example, biopsy catheter instruments have been used to retrieve myocardial tissue from within a chamber of the heart. When advancing such a biopsy catheter instrument into the heart, the physician may have difficulty in accessing and maintaining position within a particular heart chamber, such as the right ventricle. In addition, the physician may have difficulty verifying that the catheter tip portion is in fact delivered to the targeted heart chamber.

SUMMARY

Some embodiments of a biopsy system are configured to obtain a sample of tissue from an internal body site, such as a portion of myocardial tissue from a heart chamber wall. The biopsy system may include a catheter device having tissue collection jaws and an inflatable balloon disposed along a distal portion. The balloon may be inflated when the catheter device is disposed within a targeted heart chamber, such as the right ventricle, so as to maintain the position of the tissue collection jaws within the targeted chamber. Also, the biopsy system may include a pressure sensor device to detect the pressure within the heart chamber in which the tissue collection jaws are disposed. Such a pressure sensor device may verify to the physician that the tissue collection jaws are disposed within the targeted chamber.

Some or all of these embodiments may provide one or more of the following advantages. First, the biopsy system may be used in a noninvasive procedure to access the heart and retrieve a tissue sample from the heart chamber wall. Second, a physician may be able to readily access and maintain the position of the tissue collection jaws within the targeted heart chamber. Third, the biopsy system may provide data from one or more sensors that indicate to the physician the tissue collection jaws are disposed within the targeted heart chamber. Fourth, the biopsy system may be actuated within the targeted heart chamber to collect a myocardial tissue sample while the physician is provided with a visual indicator of the location of the tissue collection jaws.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 2 is a cross-sectional view of a portion of a biopsy system of FIG. 1.

FIG. 3 is a cross-sectional view of a portion of a biopsy system in accordance with other embodiments.

Like reference symbols in the various drawings indicate like elements.

DETAILED DESCRIPTION OF ILLUSTRATIVE EMBODIMENTS

Figure 1:
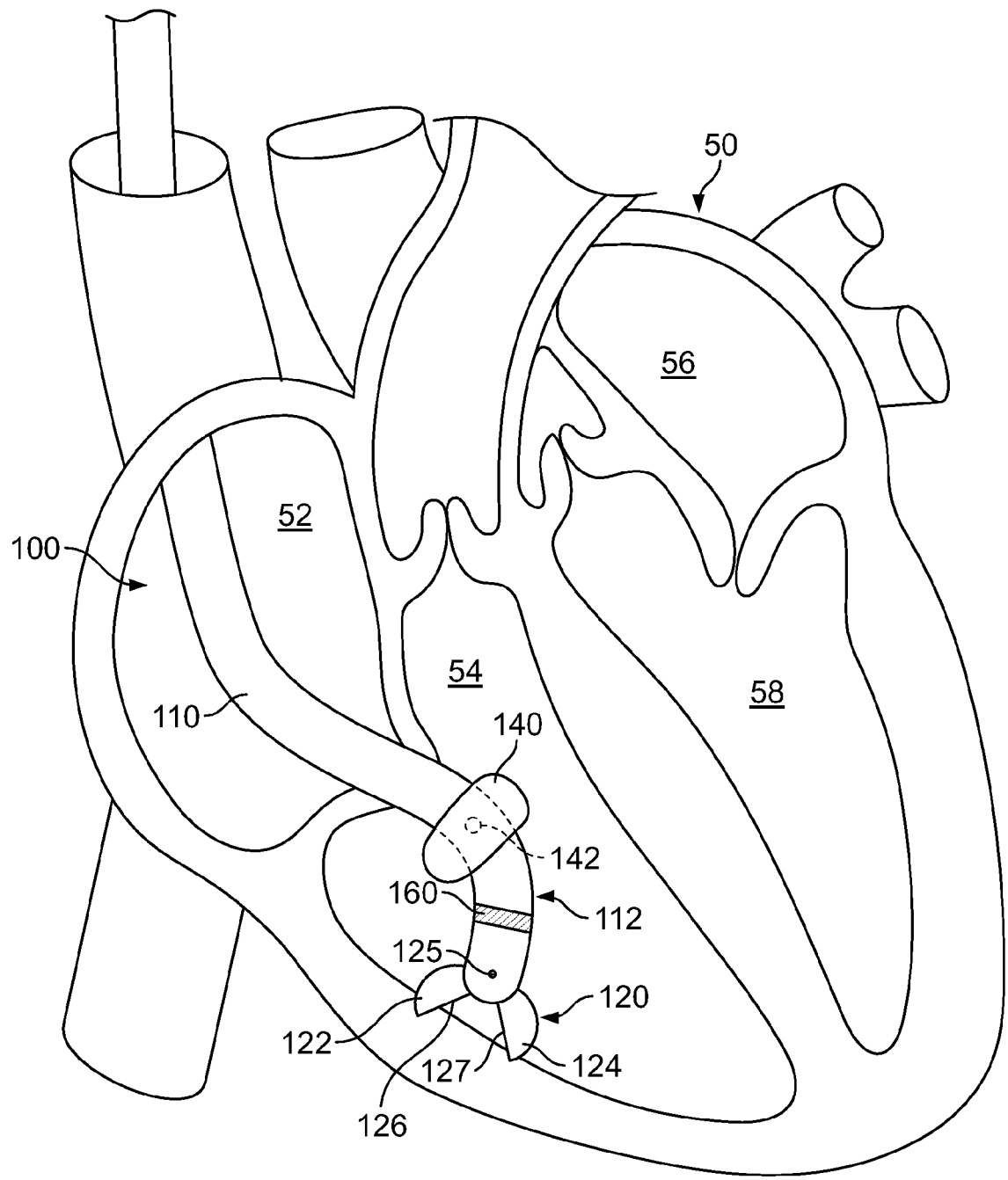
FIG. 1 is a cross-sectional view of a heart accessed by a portion of a biopsy system.
Figure 4:
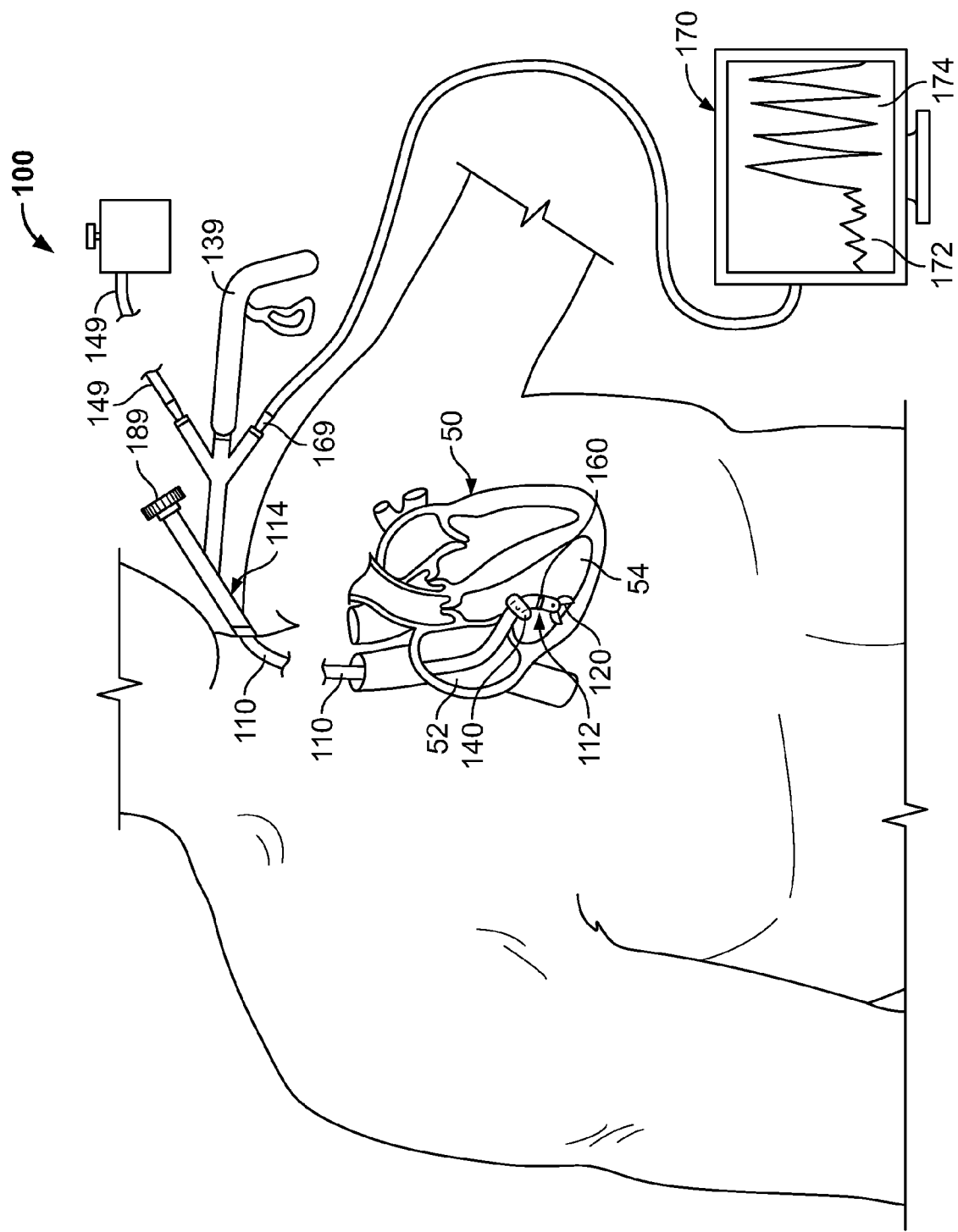
FIG. 4 is a view of a biopsy system in accordance with some embodiments.

Referring to FIG. 1, a biopsy system 100 may include catheter device 110 having an elongate body that extends between a distal portion 112 and a proximal portion 114 (refer to FIG. 4). The catheter device 110 may include one or more lumens extending to the distal portion 112 so that a number of wires, cables, rods, or fluids can individually or collectively pass through the lumens toward the distal portion. For example, the catheter device 110 may include an actuation rod or the like that can be selectively actuated by a physician to adjust the tissue collection jaws 120 disposed along the distal portion 112. In some embodiments, the elongate body of the catheter device 110 may have an outer diameter about 10 mm to about 25 mm, about 15 mm to about 24 mm, and about 20 mm to about 23 mm. It should be understood from the description herein that the catheter dimensions (e.g., length, diameter, and the like) may be selected based upon the anatomy of the patient.

In this embodiment, the tissue collection jaws 120 comprise hollow cup-shaped members 122 and 124 that are pivotally engaged together about a pivot pin 125 coupled to the distal portion 112 of the catheter device 110. The cup-shaped jaw members 122 and 124 may oppose another such that the tissue collection jaws 120 can be adjusted to a closed position in which a tissue sample (e.g., myocardial tissue) is collected within the hollow space between the closed members 122 and 124. In some embodiments, the jaw members 122 and 124 are made of stainless steel and are about 1 mm to about 6 mm in diameter, about 2 mm to about 5 mm in diameter, and about 3 mm to about 4 mm in diameter. In some circumstances, the cutting surfaces 126 and 127 of the jaw members 122 and 124 may comprise a plurality of serrated teeth to facilitate cutting of the tissue sample. In these embodiments, the serrated teeth can be configured to mated together when the jaw members 122 and 124 are in the closed position.

The biopsy system 100 may be employed to biopsy a portion of the myocardial tissue to aid in the diagnosis of a number of conditions. For example, a biopsy of myocardial tissue may be retrieved to as part of a process to diagnose cardiomyopathies (e.g., alcoholic cardiomyopathy, hypertrophic cardiomyopathy, idiopathic cardiomyopathy, ischemic cardiomyopathy, peripartum cardiomyopathy, or restrictive cardiomyopathy), myocarditis, amyloidosis, transplant rejection, or the like. In such circumstances, the myocardial tissue sample may be collected from the heart chamber wall surrounding the right ventricle 54, as shown, for example, in FIG. 1. It should be understood that, in other embodiments, the biopsy system 100 may be employed to collect the myocardial tissue sample from within other heart chambers, such as the right atrium 52, the left atrium 56, the left ventricle 58, or a combination of heart chambers.

Still referring to FIG. 1, the biopsy system 100 includes an inflatable balloon device 140 disposed along the distal portion 112 of the catheter device 110. The inflatable balloon device 140 may be in a deflated condition as the catheter device 110 is directed into the patient's body and to the targeted heart chamber (e.g., the right ventricle 54 in the embodiment shown in FIG. 1). When the distal portion 112 of the catheter device 110 is delivered to the targeted heart chamber, the balloon device 140 can be expanded to an inflated condition, as shown in FIG. 1. For example, a fluid such as pressurized air or saline can be passed through a lumen of the catheter device 110 to a fluid port 142 in communication with the balloon device 140. The fluid fills the balloon device 140 until the balloon device has reached the inflated condition. In some embodiments, the balloon device 140 may comprise a flexible material that can be repeatedly inflated and deflated. The material of the balloon device 140 may be selected from polymers including, but not limited to, polyolefin copolymer, polyester, polyethylene teraphthalate, polyethylene, polyether-block-amide, polyamide, polyimide, nylon, latex and urethane. The balloon device 140 may be made by blow molding a polymer extrusion into the desired shape. In some embodiments, the balloon device 140 may be constructed to expand to the desired shape when pressurized, but the balloon device 140 will not elastically deform substantially beyond the desired shape.

When the balloon device 140 is expanded to the inflated condition, the balloon device 140 can serve as an anchor-like device that maintains the position of the distal portion 112 in the targeted chamber (e.g., the right ventricle 54). For example, the inflated balloon device 140 may inhibit the distal portion 112 from being retracted out of the right ventricle 54 and into the right atrium 52 during the biopsy procedure. In these circumstances, the inflated balloon device 140 maybe biased by the blood flow to remain in the right ventricle 54. In addition, the inflated balloon device 140 may drag against or otherwise abut a wall of the heart chamber or the heart valve so that the distal portion 112 remains in the targeted heart chamber during the biopsy procedure. Accordingly, the balloon device 140 can be expanded to the inflated condition so as to maintain the position of the tissue collection jaws 120 within the targeted heart chamber, thereby facilitating the collection of the myocardial tissue sample from the desired location along the heart chamber wall.

Still referring to FIG. 1, the biopsy system 100 may include one or more pressure sensor devices 160 that detects the blood pressure proximal to the distal portion 112. In this embodiment, a single pressure sensor device 160 comprises a pressure transducer, such as a solid state pressure transducer, disposed along the outer surface of the distal portion 112 of the catheter device 110. For example, the pressure sensor device 160 may comprise a micromanometer device such as those produced by Millar Instruments. The micromanometer device may include a small transducer exposed to blood pressure on one side and a reference pressure on the opposite side. Blood pressure deforms the transducer resulting in a change in resistance which is translated into a pressure reading. An electrical line (described below) connected to the pressure transducer may pass through a lumen in the catheter device 110 to the proximal portion so that the transducer data signals can be transmitted to medical monitoring equipment outside the patient's body. In this embodiment, the pressure sensor device 160 is disposed along the outer portion of the catheter device 110 distally of the inflatable balloon device 140. However, it should be understood that the pressure sensor device 160 may be disposed along the outer portion of the catheter device 110 and within the inflatable balloon device 140 such that pressure fluctuations upon the balloon device 140 are sensed by the pressure sensor 160 and translated into blood pressure readings. Moreover, some embodiments of the pressure sensor device 160 may include a sensor device other than a transducer, such as a fiber optic sensor capable of detecting the blood pressure within the targeted heart chamber.

As described in more detail below, an electrical line (described below) connected to the pressure transducer may pass through a lumen in the catheter device 110 to the proximal portion so that the pressure readings can be displayed to the physician. Accordingly, the biopsy system 100 may provide data from the pressure sensor device 160 to indicate to the physician the tissue collection jaws are disposed within the targeted heart chamber. For example, the pressure sensor device 160 may indicate when the distal portion 112 passes from the right atrium 52 and into the right ventricle 54 (as shown in FIG. 1) because the blood pressure in right ventricle 54 (about 20 mmHg to about 40 mmHg, about 25 mmHg to about 35 mmHg, about 28 mmHg to about 32 mmHg, and generally about 30 mmHg) is much greater than that of the right atrium (about 0 mmHg to about 10 mmHg, about 0 to about 7 mmHg, about 0 mmHg to about 5 mmHg, and generally about 0 mmHg to about 3 mmHg). As such, the blood pressure data transmitted from the pressure sensor device 160 can be displayed to the physician so as to verify that the tissue collection jaws 120 are disposed within the targeted chamber (e.g., the right ventricle 54 in the embodiment shown in FIG. 1).

Referring now to FIG. 2, the catheter device 110 may comprise a number of longitudinally extending lumens through which wires, cables, rods, or fluid may pass. One such lumen may be occupied by an actuation device 130 that adjustably controls the tissue collection jaws 120. As previously described, the tissue collection jaws 120 can be adjusted between an opened position and a closed position so as to cut and retain a tissue sample. In this embodiment, the actuation device 130 includes a slider member 132 that can be advanced distally (refer to the arrow shown in FIG. 2) so as to pivot the jaw members 122 and 124 about the pivot pin 125 toward the opened position (as shown in dotted lines in FIG. 2). Likewise, the slider member 132 that can be retracted proximally (opposite direction of the arrow shown in FIG. 2) so as to pivot the jaw members 122 and 124 about the pivot pin 125 toward the closed position (as shown in solid lines in FIG. 2). The slider member 132 is at least partially disposed in the actuation device lumen, and an actuation rod 134 is coupled thereto. In this embodiment, the actuation rod 134 comprises a Nitinol material that is sufficiently flexible to bend with the catheter device (e.g., when the catheter device is directed through the patient's anatomy) and is sufficiently strong to transfer the adjustment forces. As such, the physician or other user may push, pull, or otherwise adjust the actuation rod 134 at the proximal portion of the catheter device 110 (e.g., using a trigger device or the like as shown in FIG. 4) so that the slider member 132 is advanced distally or retracted proximally under the control of the physician.

Another lumen extending longitudinally through the catheter device 110 may be used to deliver fluid into the balloon device 140 when inflation is required and to subsequently withdraw fluid from the balloon device 140 when deflation is required. As shown in FIG. 2, the balloon device 140 may be in fluid communication with a fluid delivery lumen 144 via one or more ports 142 along the distal portion 112 of the catheter device 110. The proximal end of the fluid delivery lumen 144 may be in fluid communication with a reservoir of pressurized air, saline, or another fluid. As such, a physician or other user may control the flow of fluid through the lumen 144 so that the fluid is delivered into the balloon device 140 for inflation purposes or is withdrawn from the balloon device for deflation purposes. As previously described, the balloon device 140 may be constructed to expand to the desired shape when pressurized, but the balloon device 140 will not elastically deform substantially beyond the desired shape. In this embodiment, the balloon device 140 is shown as having a substantially cylindrical shape when fully inflated, but other embodiments can employ a balloon device having another shape such as conical, frusto-conical, hyperbolic, spherical, rectangular, or the like.

Still referring to FIG. 2, the catheter device 110 may include a lumen extending therethrough in the form of a pressure sensor channel. The pressure sensor channel may be used in conjunction with the pressure sensor device 160. In this embodiment, an electrical wire 164 extends through the pressure sensor channel to the distal portion 112 of the catheter device. The electrical wire 164 is connected with the pressure sensor device 160 so that data signals from the pressure sensor device 160 can be communicated to the medical monitoring equipment disposed outside the patient's body (e.g., near the proximal portion of the catheter device 110). In those embodiments in which the pressure sensor device 160 includes a transducer that operates with a reference pressure, the pressure sensor channel may include a fluid (e.g., air or a liquid solution) under a predetermined pressure so as to act as the reference pressure to the transducer.

As shown in FIG. 2, the pressure sensor device 160 may have a ring-shaped body that spans along the outer surface of the distal portion 112 of the catheter device 110. In some embodiments, only a portion of the ring-shaped body may operates as a pressure transducer (e.g., that portion disposed near the pressure sensor channel). In alternative embodiments, the pressure sensor device 160 may comprise a body that does not completely encircle the catheter device 110 (e.g., may have a smaller body in the shape of a circular or rectangular sensor pad). In those embodiments, the sensor pad may comprise the pressure transducer that is disposed over the pressure sensor channel through which the electrical wire 164 passes.

In the embodiment depicted in FIG. 2, the pressure sensor device 160 is disposed distally of the balloon device 140 along the distal portion 112 of the catheter device 110. It should be understood that, in other embodiments, the pressure sensor device 160 may be disposed along the outer surface of the catheter device 110 within the balloon device 140. In these embodiments, pressure fluctuations upon the outer surface of the inflated balloon device 140 (e.g., the blood pressure acting upon the outer surface of the balloon device 140) can be sensed by the pressure sensor 160 and translated into blood pressure readings. Moreover, in alternative embodiments, the pressure sensor device 160 may be disposed along the outer surface of the catheter device 110 is a position proximal of the balloon device 140 such that the pressure sensor device 160 indicates the blood pressure in the heart chamber in which the balloon device 140 and tissue collection jaws 120 are located.

The distal portion 112 of the catheter device 110 may be steerable using one or more steering mechanisms, such as steering cables, shape memory devices, or the like. In the embodiment depicted in FIG. 2, the steering mechanism 180 comprises at least one steering cable 182 that extends through a lumen of the catheter device and is fixedly attached to a side wall of the distal portion 112 of the catheter device 110. Accordingly, the physician or other user may operate a steering control instrument (refer to FIG. 4) that can pull upon the steering cable 182 or otherwise adjust the length of the steering cable 182 to thereby cause the distal portion 112 of the catheter device to bend in a particular direction. Such a bending action permits the physician or other user to steer the catheter device 110 through the patient's anatomy and into the targeted internal site (e.g., into a targeted heart chamber such as the right ventricle 54 shown in FIG. 1). In this embodiment, the steering cable 182 comprises a Nitinol material that is sufficiently flexible to bend with the catheter device (e.g., when the catheter device is directed through the patient's anatomy) and is sufficiently strong to transfer the tension forces or other control forces.

Although a number of individual lumens have been described as extending through the catheter device, it should be understood that a single lumen may be employed to perform a plurality of functions. For example, a single lumen may serves as both the steering cable lumen (containing at least a portion of the steering cable 182) and the pressure sensor channel (containing at least a portion of the electrical wire 164). Other such multi-use lumens can be understood from the description herein.

Referring now to FIG. 3, some embodiments of a biopsy system 200 may include a pressure sensor device that operates in conjunction with the fluid filled balloon device 140. For example, the biopsy system 200 may include a pressure sensor port 262 and a pressure sensor channel 264 in fluid communication with the balloon device 140. Similar to previously described embodiments, the balloon device 140 may also be in fluid communication with a fluid delivery port 142 and a fluid delivery channel 144 through which the fluid is delivered into (and withdrawn from) the balloon device 140. Also similar to previously described embodiments, the biopsy system 200 may include tissue collection jaws 120, an actuation device 130, and a steering mechanism 180.

In the embodiment depicted in FIG. 3, the pressure sensor channel 264 may be filled with the fluid that is used to inflate the balloon device 140. Thus, when the balloon device is fully inflated, pressure fluctuations acting upon the outer surface of the balloon device 140 can be transmitted through the fluid in the pressure sensor channel 264 for detection by a pressure sensor device (e.g., a pressure transducer) disposed near the proximal portion of the catheter device (refer to FIG. 4). For example, the pressure fluctuations acting upon the fluid in the pressure sensor channel 264 may indicate when the balloon device 140 is in the right ventricle 54 because the blood pressure in right ventricle 54 is much greater than that of the right atrium 52. As such, the pressure fluctuations acting upon the balloon device 140 and transmitted to the fluid therein can be translated into blood pressure readings and can be displayed to the physician so as to verify that the tissue collection jaws 120 are disposed within the targeted heart chamber.

Referring to FIG. 4, in operation, the distal portion 112 of the catheter device may be advanced through an incision in the patient's neck, through the venous system (e.g., the jugular vein or the like), and into the patient's heart 50. The proximal portion 114 of the catheter device 110 may remain outside the patient's body so that one or more instruments can perform particular functions using the one or lumens extending through the catheter device 110. For example, as previously described in connection with FIGS. 2-3, the tissue collection jaws 120 can be adjusted between an opened position and a closed position so as to obtain a tissue sample from an internal site in the patient's body. The actuation device 130 (refer to FIG. 2 or FIG. 3) can adjustably control the tissue collection jaws 120 by moving the actuation rod 134 within the actuator lumen extending through the catheter device 110. In the embodiment depicted in FIG. 4, the actuation device 130 is controlled by a trigger device 139 that is coupled to the actuation rod 134 disposed within the actuator lumen. As such, the physician or other user may adjust the trigger device 139 to adjust the actuation rod 134 at the proximal portion of the catheter device 110. In some embodiments, the trigger device 139 can be spring loaded so as to bias the tissue collection jaws 120 into one of the opened or closed positions (e.g., the tissue collection jaws 120 are biased to remain in the closed position until the physician adjusts the trigger device 139 in the appropriate manner). In addition or in the alternative, the trigger device may include a locking mechanism to lock the tissue collection jaws 120 into one of the opened or closed positions (e.g., the tissue collection jaws 120 can be locked to remain in the closed position after the tissue sample is collected).

The proximal portion 114 of the catheter device 110 may also interact with a fluid reservoir 149 that is in fluid communication with the fluid delivery lumen 144. The reservoir 149 may be used to deliver fluid into the balloon device 140 when inflation is required and to subsequently withdraw fluid from the balloon device 140 when deflation is required. For example, the reservoir 149 may be configured to pump air, saline, or another fluid through the fluid delivery lumen 144 and into the balloon device 140 or to pump out (or vacuum) the fluid out of the balloon device 140. As such, a physician or other user may control the reservoir 149 to adjust the flow of fluid into or out of the balloon device 140.

Still referring to FIG. 4, a steering control instrument 189 may be disposed near the proximal portion 114 of the catheter device 110 so as to adjust the one or more steering cables 182 extending through the one or more corresponding steering lumens of the catheter device 110. In this embodiment, the steering control instrument 189 includes a ratchet wheel that can be turned in a first direction so as to pull upon the steering cable 182 extending to the distal portion 112 of the catheter device 110. Also, the ratchet wheel of the steering control instrument 189 can be turned in a second direction so as to extend or otherwise relieve the tension in the steering cable 182. Accordingly, the physician or other user may adjust the ratchet wheel of the steering control instrument 189 so as to bend or steer the distal portion 112 of the catheter device 110.

As previously described, the biopsy system 100 may include one or more pressure sensor devices that are capable of detecting the blood pressure of the heart chamber in which the tissue collection jaws 120 are located. In the embodiment depicted in FIG. 4, the pressure sensor device 160 comprises a pressure transducer disposed along the outer surface of the distal portion 112 of the catheter device 110. The pressure transducer is connected to the electrical line 164 (FIG. 2) that passes through a lumen in the catheter device 110 to the proximal portion 114 so that the transducer data signals can be transmitted to medical monitoring equipment 170 outside the patient's body. For example, the electrical line 164 may connect with a data cable 169 of the monitoring equipment 170 so that the transducer signals can be translated into pressure readings.

Accordingly, the biopsy system 100 may provide data from the pressure sensor device 160 to indicate to the physician the tissue collection jaws are disposed within the targeted heart chamber. For example, the pressure sensor device 160 may indicate when the distal portion 112 passes from the right atrium 52 and into the right ventricle 54 (as shown in FIG. 4) because the blood pressure in right ventricle 54 (about 20 mmHg to about 40 mmHg, about 25 mmHg to about 35 mmHg, about 28 mmHg to about 32 mmHg, and generally about 30 mmHg) is much greater than that of the right atrium 52 (about 0 mmHg to about 10 mmHg, about 0 to about 7 mmHg, about 0 mmHg to about 5 mmHg, and generally about 0 mmHg to about 3 mmHg).

The medical monitoring equipment 170 can include a display device so that the blood pressure data transmitted from the pressure sensor device 160 is viewable by the physician, thereby permitting the physician to verify that the tissue collection jaws 120 are disposed within the targeted chamber (e.g., the right ventricle 54 in the embodiment shown in FIG. 4). For example, when the distal portion 112 of the catheter device 110 is passed into the right atrium 52, the pressure readings 172 displayed on the medical monitoring equipment 170 may be much lower than the pressure readings 174 that are displayed when the distal portion 112 is advanced into the right ventricle 54.

As previously described in connection with FIG. 3, the blood pressure in the targeted heart chamber may be detected by pressure fluctuations acting upon the balloon device 140 (and the fluid inside the balloon device 140). In these embodiments, the pressure sensor channel 264 (FIG. 3) may be in fluid communication with a pressure transducer device disposed along the proximal portion 114 of the catheter device 110. This pressure transducer may be connected to the data cable 169 (FIG. 4) of the medical monitoring equipment 170 so that the data signals from the pressure transducer can be translated into pressure readings displayed to the physician.

A number of embodiments of the invention have been described. Nevertheless, it will be understood that various modifications may be made without departing from the spirit and scope of the invention. Accordingly, other embodiments are within the scope of the following claims.

What is claimed is:

1. A biopsy system for collecting a sample of heart tissue, comprising:
    a catheter device having an elongate body that extends from a proximal portion to a distal portion, the distal portion being deliverable to a targeted heart chamber;
    tissue collection jaws to obtain a sample of body tissue, the tissue collection jaws being disposed along the distal portion;
    an inflatable balloon device to maintain position of the distal portion in the targeted heart chamber when the balloon device is expanded to an inflated condition, the balloon device being disposed along the distal portion at a position proximal to the position of said tissue collection jaws when in said inflated condition, and
    a pressure sensor device to detect a blood pressure proximate to the tissue collection jaws, the pressure sensor device being coupled to the catheter device, wherein the pressure sensor device comprises a pressure transducer disposed along an outer portion of the catheter device, wherein the pressure sensor device comprises a micromanometer device that, when delivered to the targeted heart chamber, is exposed to blood pressure on one side and a reference pressure on the opposite side, and wherein the tissue collection jaws, inflatable balloon, and pressure sensor device are configured to be located within the targeted heart chamber when the distal portion of the catheter device is delivered to the targeted heart chamber.

2. The system of claim 1, wherein the catheter device includes: a fluid delivery lumen in communication with the inflatable balloon device, a pressure sensor channel in communication with the pressure sensor device, and a working channel that at least partially surrounds an actuation rod for adjusting the tissue collection jaws.

3. The system of claim 1, wherein the pressure transducer is arranged along the outer portion of the catheter device distally of the inflatable balloon device.

4. The system of claim 1, wherein the pressure transducer is arranged along the outer portion of the catheter device and within the inflatable balloon device.

5. The system of claim 1, wherein the pressure sensor device operates in conjunction with fluid in the inflatable balloon device, further comprising a pressure sensor port and a pressure sensor channel in fluid communication with the balloon device.

6. The system of claim 5, wherein pressure fluctuations acting upon an outer surface of the balloon device are transmitted through the pressure sensor channel for detection by the pressure sensor device.

7. The system of claim 1, wherein the pressure sensor device comprises a fiber optic sensor.

8. The system of claim 1, wherein data signals from the pressure sensor device are transmitted to external monitoring equipment to indicate pressure readings that are viewable to a practitioner while catheter device is being delivered to the targeted heart chamber.

9. The system of claim 8, wherein the external monitoring equipment includes a screen that displays pressure readings to indicate that the tissue collection jaws are disposed within the targeted heart chamber.

10. The system of claim 9, wherein the pressure readings in the targeted heart chamber indicate a blood pressure of about 20 mmHg to about 40 mmHg, the blood pressure in the targeted heart chamber being greater than blood pressure in an adjacent heart chamber.

11. The system of claim 1, wherein the tissue collection jaws comprise opposing concave members that are movable relative to a pivot axis so as to adjust from an opened position to a closed position, the opposing concave members at least partially defining a tissue collection space therebetween when arranged in the closed position.

12. The system of claim 11, wherein the concave members are about 1 mm to about 6 mm in diameter.

13. The system of claim 11, wherein the concave members include tissue cutting surfaces having a plurality of serrated teeth, the serrated teeth of one concave member being matable with the serrated teeth of the opposing concave member when the concave members are in the closed position.

14. The system of claim 1, the balloon device anchors the distal portion of the catheter device in the targeted chamber while the tissue collection jaws obtain the sample of bodily tissue.

15. The system of claim 14, wherein the balloon device is biased by blood flow to anchor the distal portion of the catheter device in the targeted chamber when expanded to the inflated condition.

16. The system of claim 14, wherein the balloon device abuts again at least one of a heart wall or a heart valve to anchor the distal portion of the catheter device in the targeted chamber when expanded to the inflated condition.

17. The system of claim 1, wherein when the balloon device is pressurized, the balloon device expands to a predetermined shape of the inflated condition without elastic deformation substantially beyond the predetermined shape.

18. The system of claim 17, wherein the balloon device comprises a polymer material selected from the group consisting of a polyolefin copolymer, polyester, polyethylene teraphthalate, polyethylene, polyether-block-amide, polyamide, polyimide, nylon, latex, and urethane.

19. The system of claim 17, wherein the balloon device expands to the predetermined shape selected from the group consisting of a cylindrical shape a conical shape, a frusto-conical shape, a hyperbolic shape, a spherical shape, and a rectangular prism shape.

* * * * *

UNITED STATES PATENT AND TRADEMARK OFFICE
CERTIFICATE OF CORRECTION

| | | |
|---|---|---|
| PATENT NO. | : 9,033,896 B2 | Page 1 of 1 |
| APPLICATION NO. | : 11/774804 | |
| DATED | : May 19, 2015 | |
| INVENTOR(S) | : Amir Lerman | |

It is certified that error appears in the above-identified patent and that said Letters Patent is hereby corrected as shown below:

In the claims
Column 10, line 28 (Claim 18), please delete "teraphthalate," and insert -- terephthalate, --, therefor.

Signed and Sealed this
First Day of December, 2015

Michelle K. Lee
*Director of the United States Patent and Trademark Office*